United States Patent [19]
Oldinski

[11] Patent Number: 5,419,627
[45] Date of Patent: May 30, 1995

[54] ILLUMINATED CABINET FOR SENSORY EVALUATIONS

[75] Inventor: Robert L. Oldinski, Bay City, Mich.

[73] Assignee: Dow Corning Corporation, Midland, Mich.

[21] Appl. No.: 116,743

[22] Filed: Sep. 7, 1993

[51] Int. Cl.⁶ .................................................. A47F 3/00
[52] U.S. Cl. .................................. 312/114; 312/223.5
[58] Field of Search .............................. 312/114, 223.5

[56] References Cited

U.S. PATENT DOCUMENTS

| | | | |
|---|---|---|---|
| 4,381,876 | 5/1983 | Fenwick | 312/114 |
| 4,939,625 | 7/1990 | Olson | 312/223.5 |
| 5,054,863 | 10/1991 | Amstutz et al. | 312/114 |
| 5,176,906 | 1/1993 | Lamb et al. | 424/70 |

OTHER PUBLICATIONS

J. Soc. Cosmet. Cham. 44, pp. 221–234 (Jul./Aug. 1993) "Light scattering and shine measurements of human hair: A sensitive probe of the hair surface" by Charles Reich and Clarence R. Robbins.

*Primary Examiner*—Timothy S. Thorpe
*Assistant Examiner*—William Wicker
*Attorney, Agent, or Firm*—James L. DeCesare

[57] ABSTRACT

A cabinet having top, bottom, side, and back walls, and a door for closing the cabinet. A support rod is positioned in the cabinet, and a hair tress is mounted on the support rod. The cabinet interior is illuminated by lamps, and a control panel with a switch governs the supply of electric power delivered to the lamps, for adjusting the intensity of light emitted from the lamps.

10 Claims, 1 Drawing Sheet

ILLUMINATED CABINET FOR SENSORY EVALUATIONS

BACKGROUND OF THE INVENTION

This invention is directed to an article of manufacture in the form of an illuminated cabinet, which may be used in conjunction with a sensory evaluation program, or for in-house laboratory scale testing, of new and promising hair care materials on virgin human hair tresses.

Often, new personal care products for application to the hair, such as shampoos, conditioners, fixatives, and permanent waves, are subjected to rigid screening "in-house" on a laboratory scale, or by the use of trained panelists in a program of sensory evaluation. Typically, virgin human hair tresses are treated with the new and promising products, and evaluated and screened based on observed benefits such as shine, feel, resistance to wet and dry combing, tangling, "fly-away", and curl retention.

Differences in various new and promising hair treating products can be easily detected and evaluated much more expeditiously, if the tresses are observed under the proper lighting conditions.

Thus, in U.S. Pat No. 5,176,906 which issued Jan. 5, 1993, for example, there is disclosed a certain fluorescent organosilicon compound, which when applied to the hair, can be examined under a source of ultraviolet light for fluorescence, for the purpose of determining the extensiveness of deposition of the fluorescent organosilicon compound on the hair.

The article of manufacture of the present invention provides a convenient examination tool for use in conjunction with such examination procedures.

SUMMARY OF THE INVENTION

The present invention relates to a sensory evaluation cabinet which has a door for opening and closing the cabinet, and a support rod in the upper portion of the cabinet. The support rod assists in exposing a tress of hair to illumination from one or more lamps which are mounted in the interior of the cabinet. Electric power is delivered to the lamps, and the lamps are controlled by a switch interconnected with the electric power supply. The switch governs the supply of electric power to the lamps, so that the light intensity from the lamps onto the hair tresses can be adjusted.

This tool can be employed in a simple fashion by panelists trained under a sensory evaluation program, or by scientific personnel for laboratory scale evaluation, of hair care materials on human hair. For example, it can be used by panelists to determine visually the level of shine on hair tresses.

These and other features, objects, and advantages of the present invention will become more apparent from a consideration of the following detailed description thereof.

DETAILED DESCRIPTION OF THE INVENTION

Figure 1:
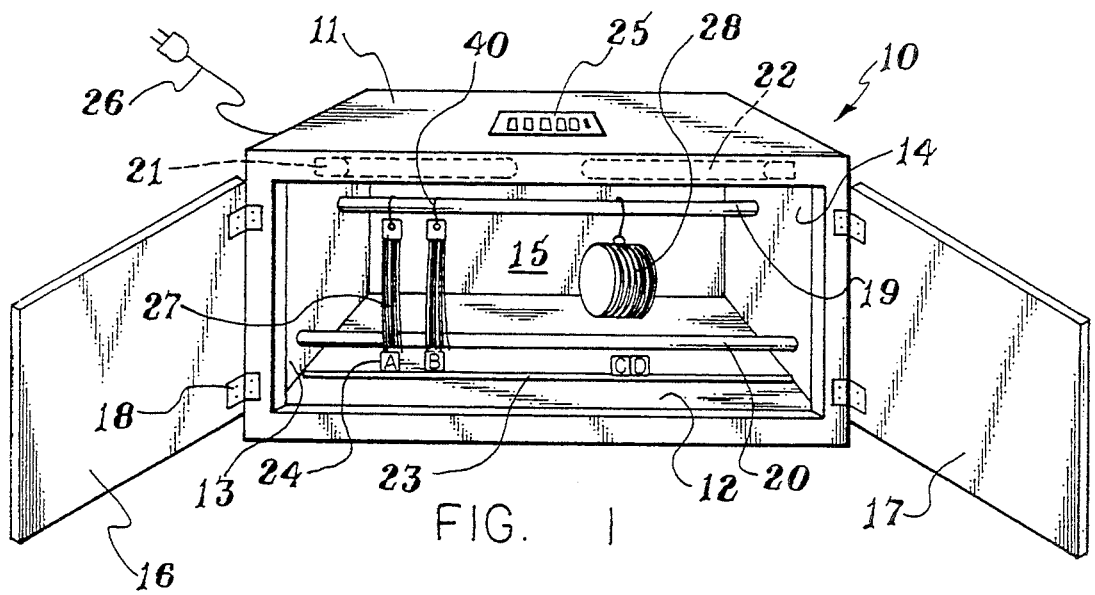
FIG. 1 is a pictorial representation and a front view of the evaluation cabinet of the present invention.

With reference to FIG. 1, there will be seen a cabinet shown generally by the numeral 10, having a top wall 11, a bottom wall 12, a pair of side walls 13 and 14, and a back wall 15. A pair of doors 16 and 17 are each mounted by hinges 18, and attached to cabinet 10, for opening and closing the cabinet 10.

A first support rod 19 is positioned in the upper portion of the cabinet 10, and a second support rod 20 is located in the lower portion of cabinet 10. Both support rods 19 and 20 extend between the side walls 13 and 14 of the cabinet 10 above the bottom wall 12. Hooks 40 are used in conjunction with support rod 19 for mounting a number of hair tresses 27 on support rod 19. The hair tresses 27 are supported at their lower ends by support rod 20.

Illumination for examining the hair tresses 27 is supplied to the interior of the cabinet 10 by a pair of lamps 21 and 22. The lamps can each be either incandescent lamps or fluorescent lamps. Typically, a clear, tubular, 60 watt, 120 volt, incandescent lamp is employed. However, when it is desired to examine the hair tresses 27 under fluorescent lighting, fluorescent lamps are employed, in which case a suitable ballast device may be required, as a portion of the electric circuitry used to power the lamps. In any event, electric power is delivered to the lamps 21 and 22 by means of an electric cord 26, which is plugged into a suitable 120 volt outlet.

A control panel 25 is mounted on the top wall 11 of cabinet 10. The control panel 25 is shown in detail in FIG. 1A, and can be seen to include a witch 35 for turning the lamps 21 and 22 "ON" and "OFF". Five push buttons 36 are arranged in the switch 25, for varying and adjusting the intensity of light emitted from the lamps 21 and 22. Each push button 36 has a red light 36A associated with it, and the lights 36A provide a visual indication of the degree of light intensity which is being used in the cabinet.

Figure 1A:
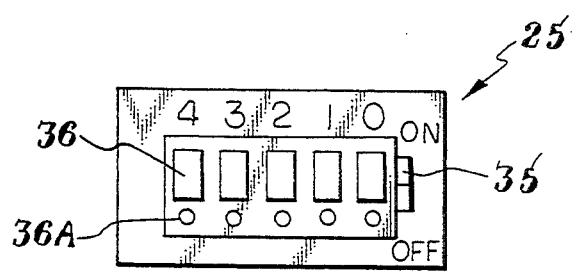
FIG. 1A is a pictorial representation of only a portion of the cabinet of FIG. 1, but showing the electrical control panel and switch in more detail.

Each push button 36 can be labelled with numerals varying from "0 to 4" as shown in FIG. 1A. The numerals are used for indicating various degrees of light intensity. For example "0" can be assigned the lowest value of no light, and "4" the highest value of the most intense light. Such control panels, switches, and associated push buttons, lights, and electric circuitry, are features well known in the art.

As is apparent form FIG. 1, the lamps 21 and 22 are each mounted on a side wall 13 and 14 of the cabinet 10, respectively, and extend into the interior of the cabinet 10 from the side walls 13 and 14. Preferably, a surface coating, such as flat black paint, is applied to the interior of the top, bottom, side, and back walls 11-15 of cabinet 10. The flat black paint is also applied to the interior of the cabinet doors 16 and 17. The flat black surface coating reduces the level of glare reflected from the lamps 21 and 22 by the interior surfaces of the cabinet. The cabinet 10 may be constructed of wood, and if desired, the exterior surfaces of the cabinet are covered with black Formica, in order to enhance its appearance.

The bottom walls 12 of the cabinet includes a laterally extending slot 23, and a plurality of upright movable coded labels 24 are arranged in slot 23. The labels 24 are movable along the slot 23, between the side walls 13 and 14 of the cabinet, and each coded label 24 bears on its surface a different visible indicia, such as a letter of the alphabet.

Figure 2:
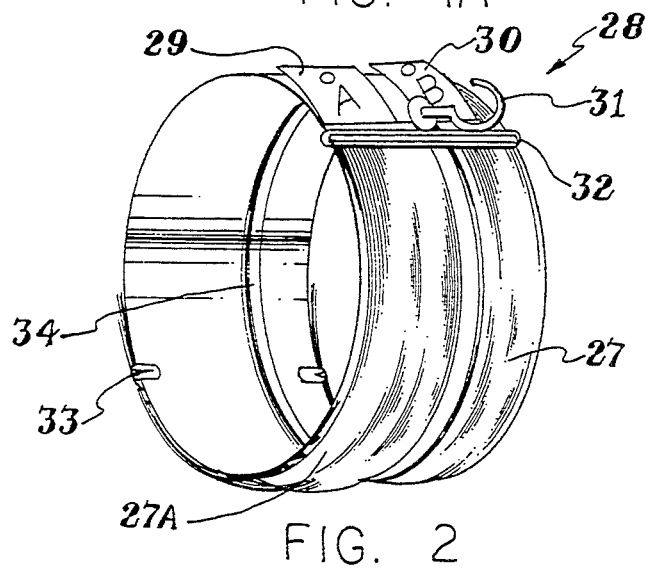
FIG. 2 is a pictorial isometric representation of a roller-type plastic cylinder used in FIG. 1, and showing the plastic cylinder carrying two hair tresses in more detail.

With reference to FIGS. 1 and 2, it will be seen that hair tresses 27 can also be arranged in the cabinet 10 for evaluation by the sensory panelist in the form of a roller. Thus, the tresses 27 can be rolled and mounted on a plastic cylinder 28. The plastic cylinder 28 includes a hook 31 for hanging the plastic cylinder 28 containing the tresses 27 onto the upper support rod 19. Any suitable plastic may be used for constructing the plastic cylinder 28, such as polyethylene, polypropylene, or polyvinyl chloride. The plastic cylinder 28 can be painted with a flat black paint to reduce glare.

The hair tresses 27 are maintained on the plastic cylinder 28 by at least one removable flexible band 32. The removable flexible band extends laterally along the exterior surface of the plastic cylinder 28, from one edge of the cylinder to the other edge. The flexible band 32 includes a knob 33 on each end which extends around the edge of the cylinder, and projects into the interior of the plastic cylinder 28. The function of the knobs 33 is to secure the hair tresses 27 and the flexible band 32 to the plastic cylinder 28. Any of the plastic materials noted above may be used for constructing the flexible bands 32. The hair tresses 27 can be simply wound around the exterior surface of the plastic cylinder 28, and one or more of the flexible bands 32 are snapped into position on the plastic cylinder 28 to hold the hair tresses 27 in place.

The plastic cylinder 28 in FIG. 2 can be seen to include one or more circumferentially extending grooves 34, which are machined or molded in the exterior surface of the plastic cylinder 28. The function of the groove 34 is to assist in positioning and maintaining the individual hair tresses 27 on the surface of the plastic cylinder 28.

Each hair tress 27 in FIG. 2 includes a square plastic tab 29 which has an opening 30 at one end of the plastic tab 29. A hook 40 is extended into the opening 30 in the square plastic tab 29, and the hook 40 is used as shown in FIG. 1, for attaching the square plastic tab 29 and the hair tress 27 onto the upper support rod 19. The hair tress 27 may be taped or glued to one side of the square plastic tab 29. When the hair tresses 27 are rolled as shown in FIG. 2, the hair tresses 27 with their attached square plastic tabs 29 are simply wound about and secured to the plastic cylinder 28, as illustrated. In the rolled condition, hook 31 rather than hook 40, is used to display the hair tresses for evaluation.

While it is considered that the standard testing protocols for hair tress evaluation are known to those skilled in the art, an example of such a standard protocol, and its requirements, is set forth below. The following methodology should enable those skilled in the art to better comprehend the utility of the cabinet of the present invention.

Dark brown "virgin" European human hair is typically used for testing shampoos, for example. A master hank of hair, about eight inches in length, is subdivided into a series of individual hair tresses. Each tress weighs about 2.5 grams. The top one inch portion of the hair tress is trimmed and glued to the 2"×2" plastic tab 29 using DUCO CEMENT ®. The cement is allowed to dry, and the hair tress is combed and trimmed, to a length which allows about six inches of hair to extend below the bottom of the plastic tab 29. Each "virgin" tress is rinsed for thirty seconds with forty degree Centigrade tap water.

The tress is shampooed and lathered with two milliliters of a fifty percent solution of PRELL ® shampoo for sixty seconds, by stroking the tress downwardly. The tress is rinsed for sixty seconds with tap water. Excess water is removed from the trees by passing the trees between the index and middle fingers. Instead of employing a commercial brand shampoo for treating the "virgin" tress, there may be used a blank shampoo. The blank shampoo is prepared by combining 450 grams of ammonium lauryl sulfate (STANDAPOL A—30 percent active), with 450 grams of distilled water. The tress is then hand combed, and evaluated using the INSTRON "WET" and the INSTRON "DRY" COMBING procedures.

INSTRON COMBING is an industry recognized test for determining hair conditioning, by the ease of wet combing and the ease of dry combing. The test employs an IONSTRON strain gauge, which is equipped to measure the force required to comb the hair. Conditioning performance is based on the ability of a particular hair treating formulation, such as a shampoo or a hair conditioner, to reduce the force required to comb the hair with the INSTRON strain gauge. The force is reported as Average Combing Load (ACL). The lower the (ACL) value, the better is the conditioning effect imparted by the formulation being tested. Typically, (ACL) base lines are initially established with "untreated" tresses.

The Average Combining Load (ACL) is defined as the area under the force curve, divided by the length or distance travelled by the INSTRON comb. This number is reported in grams or kilograms of force. The effectiveness of a treatment is the percent change in (ACL) after treatment, and this value is calculated as % Change ACL=treated hair ACL—untreated hair ACL×100%/untreated ACL.

An effective treatment is a negative number. A positive number indicates that the hair is more difficult to cob than in its untreated state.

For tests involving a conditioning shampoos, the hair tress is rinsed with tap water at 40° C. for thirty seconds. The test shampoo is applied to the tress in the amount of 0.5 milliliters, and lathered for thirty seconds by stroking the tress downwardly. The tress is rinsed for thirty seconds with 40° C. tap water, and 0.5 milliliters of the test shampoo are applied to the tress for a second time, and lathered for thirty seconds by stroking the tress downwardly. The tress is rinsed for thirty seconds with 40° C. tap water, and excess water is removed by passing the tress between the index and middle fingers.

For tests involving a hair conditioner, the hair tress is rinsed with tap water at 40° C. for thirty seconds. The test conditioner is applied to the tress in the amount of one milliliter, and the tress is stroked for thirty seconds. The tress is rinsed for thirty seconds with 40° C. tap water, and excess water is removed by passing the tress between the index and middle fingers.

According to the INSTRON WET COMBING method, each hair tress is soaked for 15–30 minutes in distilled water. Excess water is removed by passing the tress through the index and middle fingers. The tress is untangled by combing the tress by hand three times. The tress is retangled by dipping the tress in distilled water three times, and excess water is removed by passing the tress through the index and middle fingers twice.

The tress is placed on a hanger and INSTRON combed. The results of this INSTRON WET COMB- ING test can be more readily evaluated, by hanging the treated tresses in the cabinet 10 of the present invention.

According to the INSTRON DRY COMBING method, each hair tress is stored overnight in a constant environment to normalize the water content of the hair. The tress is untangled by combing the tress by hand three times. The tress is retangled by swirling the tress three times clockwise, and three times counter-clockwise. The tress is placed on a hanger and INSTRON combed.

The results of the INSTRON DRY COMBING test can be more readily evaluated, by hanging the treated tresses in the cabinet 10 of the present invention.

Other variations and modifications may be made in the structures described herein without departing from the essential features and concepts of the present invention. The forms of the invention described herein are exemplary only and are not intended as limitations on the scope of the invention as defined in the appended claims.

That which is claimed is:

1. An article of manufacture comprising a cabinet having top, bottom, side, and back walls; at least one door for closing the cabinet; a support rod positioned in the upper portion of said cabinet, the support rod extending between the side walls of the cabinet; means for mounting a tress of hair on said support rod; means for illuminating the interior of the cabinet; means for delivering electric power to the illuminating means; and a control panel mounted on said cabinet, the control panel including switch means interconnected with said electric power delivering means for governing the supply of electric power being delivered to the illuminating means, and for adjusting the intensity of light which is being emitted from the illuminating means.

2. An article of manufacture according to claim 1 in which the illuminating means is a lamp selected from the group consisting of incandescent lamps and fluorescent lamps, the lamp being mounted on at least one side wall of the cabinet and extending into the interior of the cabinet from the one side wall.

3. An article of manufacture according to claim 1 further including a surface coating applied to the interior of the top, bottom, side, and back walls of the cabinet, and to the interior of the cabinet door, for reducing the level of glare reflected from the illuminating means by the interior surfaces of the cabinet.

4. An article of manufacture according to claim 1 in which the bottom wall of the cabinet includes a laterally extending slot therein; and a plurality of upright movable coded labels arranged in the slot, the coded labels being movable along the slot between the side walls of the cabinet, each coded label bearing on its surface a different visible indicia.

5. An article of manufacture according to claim 1 further including a human hair tress attached to said mounting means.

6. An article of manufacture according to claim 5 in which the mounting means is in the form of a square tab which has an opening therein; a hook extending into the opening in the square tab and attaching the square tab onto the support rod; the hair tress being taped to one side of the square tab.

7. An article of manufacture according to claim 5 in which the mounting means is a cylinder including a hook for attaching the cylinder onto the support rod.

8. An article of manufacture according to claim 7 in which the cylinder includes at least one removable flexible band extending laterally along the exterior surface of the cylinder from one edge of the cylinder to the other edge of the cylinder, and a knob on each end of the band extending around the edge of the cylinder and into the interior of the cylinder for securing the band to the cylinder.

9. An article of manufacture according to claim 8 in which the hair tress is wound around the exterior surface of the cylinder and beneath the flexible band.

10. An article of manufacture according to claim 9 in which the cylinder includes at least one circumferentially extending groove in the exterior surface of the cylinder for positioning the hair tress on the cylinder.

* * * * *